May 16, 1972 W. H. DANIEL Plant Pat. 3,175
KENTUCKY BLUEGRASS (POA PRATENSIS)
Filed July 7, 1969
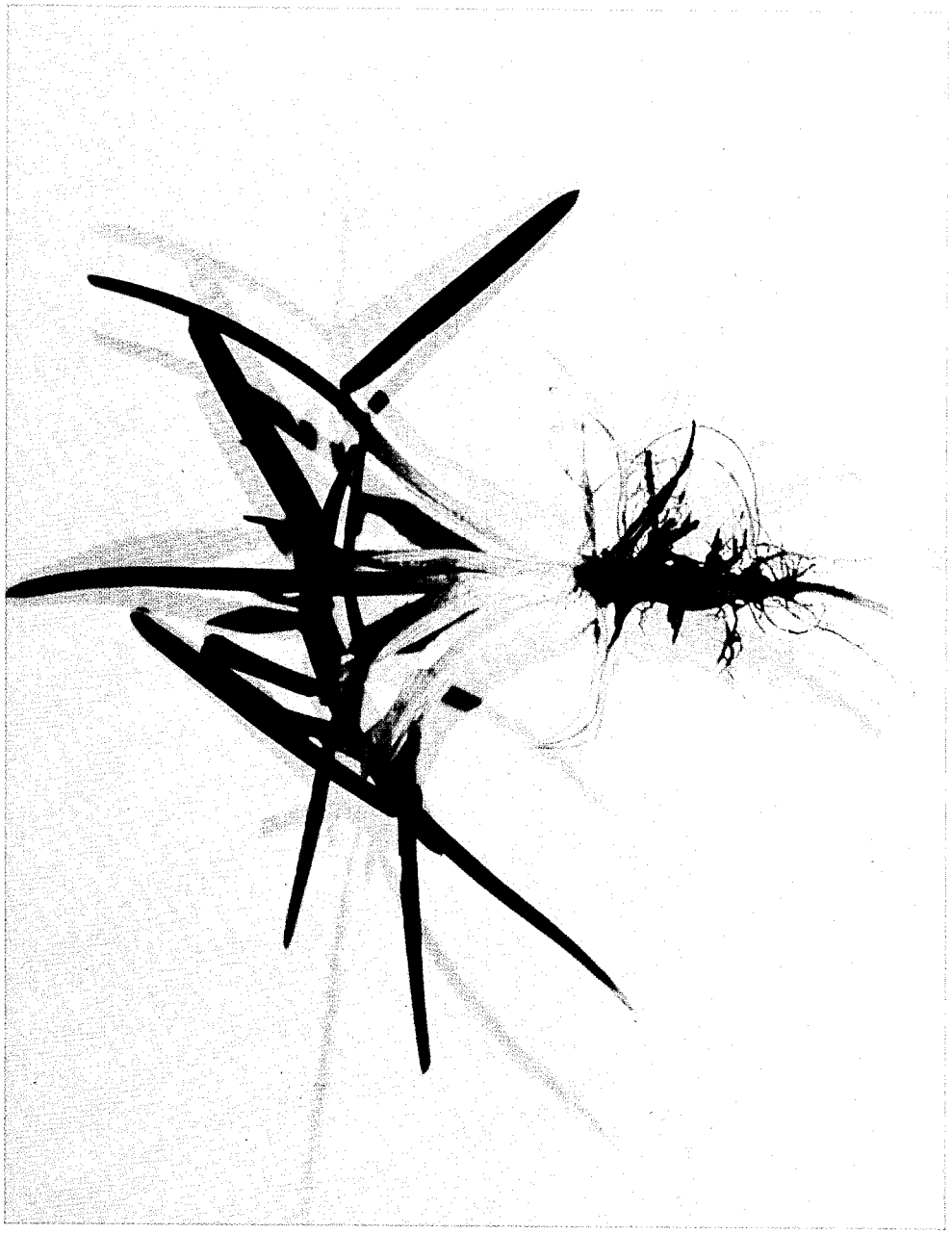
INVENTOR.
WILLIAM H. DANIEL
BY: J. R. Moulitt
ATTORNEY.

United States Patent Office

Plant Pat. 3,175
Patented May 16, 1972

3,175
KENTUCKY BLUEGRASS (*POA PRATENSIS*)

William H. Daniel, West Lafayette, Ind., assignor to Purdue Research Foundation

Filed July 7, 1969, Ser. No. 839,731
Int. Cl. A01h *5/00*
U.S. Cl. Plt.—88 1 Claim

This invention relates to a new and different Kentucky bluegrass, *Poa pratensis,* designated as 16–BB–56.

It has excellent resistance to leafspot, stripe smut and steam rust, plus low growth and dark color.

As history, it is a seedling, B56, from the 16B parent (a selection from No. 16 Fairway of Chicago Golf Club, which has produced many variable progeny). From a greenhouse planting of Oct. 1, 1962, plant 56 (of 234 increased) at 75 days showed 7 leaves averaging 9 cm. in height, and 3 rhizomes—about average. At 100 days it rated 4 for color (1-dark—9-light), leaf width 5 (1 narrow), growth habit 3 (1 most vigor), and showed excellent powdery mildew resistance, rating 2 (1 free—9 severe).

As a mature plant its seed production is slower than Dwarf. It rated 6.3 late maturing (where 1-earliest to 9-latest of all plants). The seedhead (19″ at Lafayette, Indiana, tends to be higher than Dwarf, 15″). The panicle is wide and low in character with well developed heavy stems and heavy seed.

It is also additive to the qualities of Dwarf and AQ6 and RI–10, each described in co-pending U.S. plant patent application Ser. Nos. 839,731, 839,732 and 839,734, respectively.

This is the only selection as yet out of thousands of variations observed from original 16B. It has been over 80% of our breeding stock. The apomictic dark green low growing is unique and from entirely different germ plasm than the other lines described in the afore-said co-pending U.S. plant patent applications.

Comparison of 16–BB–56, with Dwarf, AQ6 and RI–10 are as follows:

| | Dwarf | AQ6 | 16–BB–56 | RI–10 |
|---|---|---|---|---|
| Plants, number of | 285 | 39 | 35 | 200 |
| Years when data was taken | 1965–68 | 1966 | 1966–68 | 1965–68 |

| Character | Dwarf | AQ6 | 16–BB–56 | RI–10 | Comment |
|---|---|---|---|---|---|
| Leaf height, inches | 7.2 | 5.2 | 8.5 | 6.6 | Low. |
| Spread rating, 1 most | 5.9 | 5.1 | 4.7 | 5.8 | Only medium. |
| Color-rating, 1 greenest | 3.3 | 1.3 | 3.7 | 3.2 | Dark green. |
| Stripe smut resistance 1 best | 1 | 1 | 1 | 1 | None observed anywhere. |
| Maturing of seedtime rating, 1 earliest | 5.4 | 4.5 | 5.5 | 4.8 | Medium late. |
| Quality of seed rating 1 most | 5.7 | 4.2 | 3.8 | 4.4 | About average. |
| Seedhead height, inches | 14.2 | 14.5 | 19.3 | 15.2 | In lower 50%. |

NOTE.—Ratings range: 1 most desired; 3 is good; 5 is average; 9 least desired.

The plant was transplanted outside in spring 1963, and in October sprigs were removed and planted as a 3′ x 5′ plot.

As mowed turf, the 16–BB–56 rated 3 for early spring greenup, density at high cut (2″) was good density at low cut (.75″) was fair. The summertime leafspot, *H. vagans,* rating of among 4 (1 free) was good. The spring leafspot, *H. sativium,* rating of 1 was excellent (1 free—9 severe).

Resistance to stem rust *Puccinia graminis* for 16–BB–56 was rating of 2.2 for 90 plants (field 9A3, 1966) when Windsor was 9.0 or worst of all entries. For this specific reason it is included as one of 4 lines for incorporation in Sodco Variety.

This unique seedling (obviously different from 16B parent and many of its offspring) is quite apomictic, which provides uniform seedlings. In 10B1 Summer 1968 15 of 15 seedlings were uniform in 1 row and 14 of 15 uniform in second row. As a plant 16–BB–56 has wide leaves (4–7 mm.) of dark green color, and short leaves 4–8″ in unmowed space plants. The wide leaf angle, stiff, thick leaf and tolerance to disease gives characteristics desired in turf.

Many distinctive characteristics of 16–BB–56 as respects most other bluegrasses are similar to Dwarf, and except where noted otherwise in the foregoing table, it may be assumed that the distinctions of Dwarf as respects other bluegrasses are similar for 16–BB–56.

Of initial seed increase of 90 seedlings of 16–BB–56

2 plants were preferred in low growing
8 plants were preferred in medium growing of 90 seedlings.

From this (90 seedlings, one representative plant) seedling 20–72 was chosen as the increase plant. The seed of each desired plant was hand harvested, bagged and stored. The plant 20–72 was chosen as representative, and not new or different from 16–BB–56.

Seed, 3 (good); Spread, 4; Rust, 1 (best); Seed height, 10; Seed quantity, Medium; Seed maturity, 6 (late).

I claim:

1. A new and distinct variety of bluegrass plant, substantially as described and illustrated.

No references cited.

ROBERT E. BAGWILL, Primary Examiner